(12) United States Patent
Shimizu

(10) Patent No.: US 7,191,075 B2
(45) Date of Patent: Mar. 13, 2007

(54) DATA COLLECTION SYSTEM

(75) Inventor: Hideki Shimizu, Hannou (JP)

(73) Assignee: Citizen Watch Co., Ltd., Tokyo (JP)

( * ) Notice: Subject to any disclaimer, the term of this patent is extended or adjusted under 35 U.S.C. 154(b) by 0 days.

(21) Appl. No.: 10/492,126

(22) PCT Filed: Oct. 22, 2002

(86) PCT No.: PCT/JP03/10964

§ 371 (c)(1),
(2), (4) Date: Apr. 7, 2004

(87) PCT Pub. No.: WO03/036583

PCT Pub. Date: May 1, 2003

(65) Prior Publication Data

US 2005/0075822 A1   Apr. 7, 2005

(30) Foreign Application Priority Data

Oct. 23, 2001   (JP)   ............................. 2001-324273

(51) Int. Cl.
*G06F 19/00* (2006.01)

(52) U.S. Cl. ........................................ 702/62; 600/300

(58) Field of Classification Search .................. 702/32, 702/62, 80, 93, 98, 99, 119, 120, 122, 130, 702/131, 168, 177, 183, 187, 188, 189; 600/300, 600/323; 340/825.52
See application file for complete search history.

(56) References Cited

U.S. PATENT DOCUMENTS

| 4,973,957 | A | * | 11/1990 | Shimizu et al. ........ 340/825.52 |
| 5,339,821 | A | * | 8/1994 | Fujimoto ..................... 600/513 |
| 5,410,471 | A | * | 4/1995 | Alyfuku et al. ............. 600/300 |
| 5,462,051 | A | * | 10/1995 | Oka et al. .................... 600/300 |
| 6,074,345 | A | * | 6/2000 | van Oostrom et al. ...... 600/300 |
| 6,330,426 | B2 | * | 12/2001 | Brown et al. ........... 434/307 R |
| 6,456,883 | B1 | * | 9/2002 | Torgerson et al. ............ 607/34 |
| 6,518,745 | B2 | * | 2/2003 | Kim et al. ................ 324/158.1 |
| 6,662,032 | B1 | * | 12/2003 | Gavish et al. .............. 600/323 |
| 2002/0013517 | A1 | * | 1/2002 | West et al. ................. 600/300 |
| 2003/0158707 | A1 | * | 8/2003 | Doi ............................ 702/187 |

FOREIGN PATENT DOCUMENTS

| JP | 10-161741 | 6/1998 |
| JP | 11-197121 | 7/1999 |
| JP | 3053091 | 4/2000 |
| JP | 2000-196627 | 7/2000 |

OTHER PUBLICATIONS

First Examination Report Application No. 028063325, issued Jul. 22, 2005 for corresponding Chinese Patent Application No. 2000-196627 with English Translation.

* cited by examiner

*Primary Examiner*—Marc S. Hoff
*Assistant Examiner*—Mohamed Charioui
(74) *Attorney, Agent, or Firm*—Smith, Gambrell & Russell, LLP (57) ABSTRACT

If a power switch of any one measuring device selected from a plurality of measuring devices (10a to 10n) is turned on, identification information for the selected measuring device is transmitted to a data collection apparatus (100). The data collection apparatus (100) identifies the selected measuring device by the received identification information, and informs a user of the way of using the measuring device by means of voices, screen display, etc.

12 Claims, 5 Drawing Sheets

DATA COLLECTION SYSTEM

TECHNICAL FIELD

The present invention relates to a data collection system in which data measured by means of a plurality of measuring devices are collected by means of a data collector.

BACKGROUND ART

Recently, an at-home healthcare system has been spreading to be used for domestic healthcare. An example of the system is described in Japan Patent Application Laid-Open No. 3053091. This at-home healthcare system comprises a plurality of healthcare measuring devices, including a sphygmomanometer, clinical thermometer, weighing machine, body-fat meter, electrocardiograph, blood sugar tester, etc., which serve to measure heath data, and a terminal unit that receives the health data transmitted from these healthcare measuring devices. The health data are transmitted from this terminal unit to external terminals in hospitals, health centers, caregiving centers, etc. through communication networks.

This at-home healthcare system can be supposed to constitute a data collection apparatus, since it is composed of a plurality of types of measuring devices (healthcare measuring devices) and a data collection apparatus (terminal equipment) that receives and stores identification information and measured values from the measuring devices.

It is unreasonable, in general, to require a user accurately to grasp the method of using any of a large number of types of measuring devices that constitute the data collection apparatus. If the user fails correctly to manipulate the selected measuring device or if the selected measuring device fails to operate correctly, the user must be immediately informed of this situation and made properly to cope with it.

However, the conventional data collection apparatus cannot fully enjoy a function to give guidance as to the way of using the measuring device selected by the user or a function to give information when the user fails correctly to manipulate the selected measuring device or when the selected measuring device fails to operate correctly.

DISCLOSURE OF THE INVENTION

The object of the present invention is to provide a data collection system which can be handled with ease even in a case where it is necessary for a data collection apparatus, which stores data transmitted from measuring devices, to identify the measuring device to be used for measurement, out of a plurality of measuring devices, before the measurement.

In order to achieve the above object, a data collection system according to the present invention comprises a plurality of measuring devices capable of transmitting identification information and measured values to another device and a data collection apparatus designed to receive and store the identification information and measured values transmitted from the measuring devices, and gives guidance as to the way of using the measuring device corresponding to the received identification information in accordance with the received identification information.

The present invention may assume the following aspects.

The identification information is transmitted by manipulating the measuring device in a predetermined manner.

The identification information is transmitted as any other predetermined manipulation than the transmission of the identification information is carried out for the measuring device.

The identification information is transmitted by carrying out a manipulation for executing measuring operation for the measuring device.

The identification information is transmitted by switching on the measuring device.

The identification information is transmitted by carrying out a manipulation for starting the measuring operation of the measuring device.

The identification information is added to the measured value as it is transmitted.

The data collection apparatus selects one measuring device from among the measuring devices in accordance with the received identification information and is brought to a reception state in which the apparatus receives only the measured value transmitted from the selected measuring device. This selection is canceled by receiving the measured value.

The selected measuring device transmits its identification information in addition to the measured value, while the data collection apparatus receives the measured value only when the identification information added to the measured value is identical with the identification information representative of the selected measuring device.

The data collection apparatus selects one measuring device from among the measuring devices in accordance with the received identification information, and gives information to prompt measurement for the selected measuring device if no identification information is received from the selected measuring device within a first time subsequent to the selection of the measuring device.

The data collection apparatus cancels the selection of the measuring device if no identification information is received from the selected measuring device within a second time subsequent to the passage of the first time.

The measuring device has an automatic power-off function to turn off the power automatically if no operation is carried out within a given time after the power is turned on. The time for the execution of automatic power-off operation is adjusted to the point of time after the passage of the first time.

According to the present invention arranged in this manner, the data collection apparatus can identify one of the measuring devices that serves for the measurement before the measurement and inform the user of the method of using the identified measuring device by means of voices, screen display, etc. Thus, a user-friendly data collection system can be constructed.

BEST MODE FOR CARRYING OUT THE INVENTION

Figure 1:
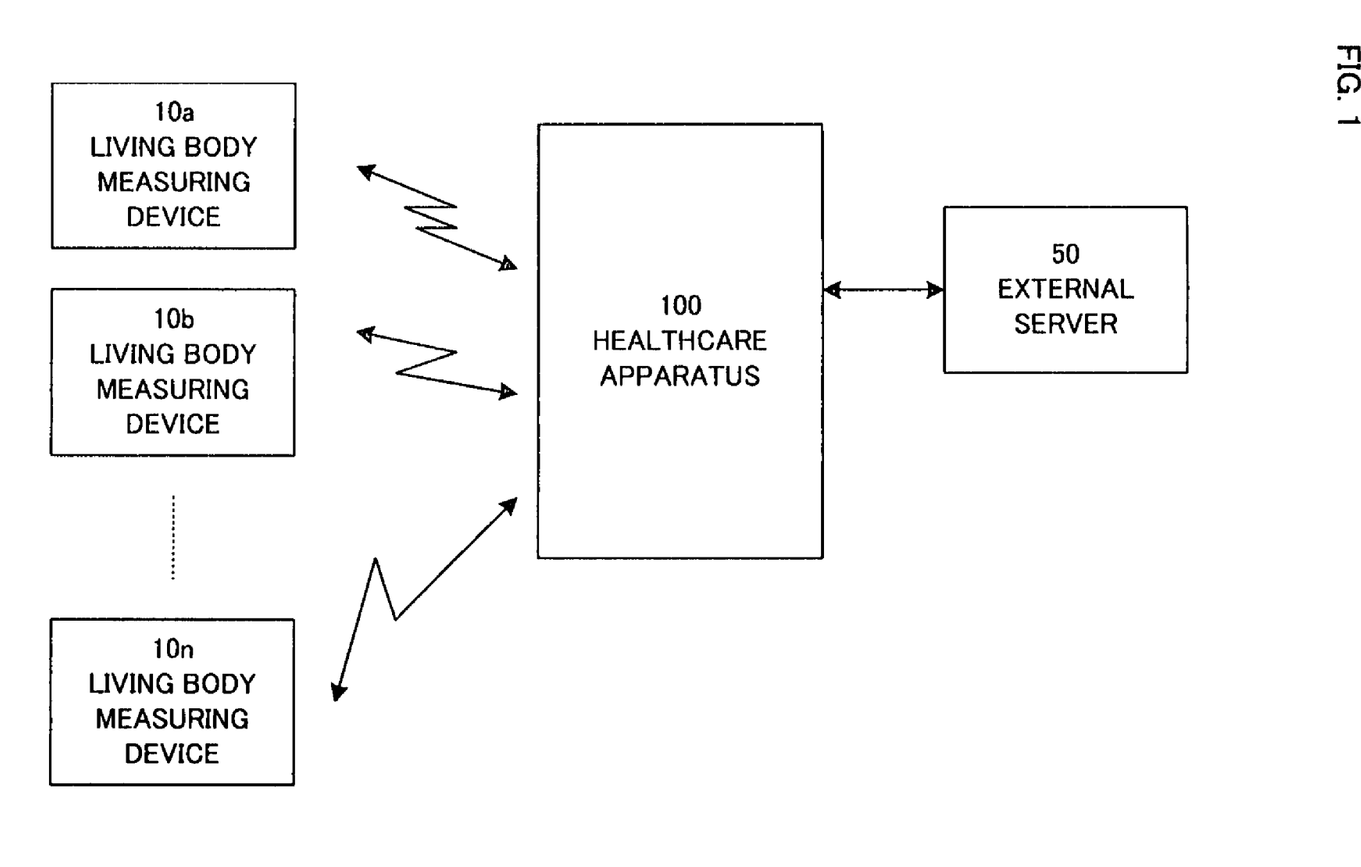
FIG. 1 is a block diagram showing an outline of a healthcare system to which a data collection system according to the present invention is applied.

FIG. 1 shows an outline of a healthcare system to which a data collection system according to the present invention is applied. This healthcare system is used by an at-home user to measure a plurality of living body data, transmit them to a hospital or caregiving center, and use them for healthcare.

In FIG. 1, reference numerals 10a to 10n denote living body measuring devices for measuring the living body data, such as a sphygmomanometer, weighing machine, body-fat meter, clinical thermometer, etc. Reference numerals 100 and 50 denote a healthcare apparatus and an external server, respectively.

The living body measuring devices 10a to 10n and the healthcare apparatus 100 are used in the user's home, while the external server 50 is set in a hospital, caregiving center, etc. The living body measuring devices 10a to 10n and the healthcare apparatus 100 can transmit to and receive data from one another by radio communication. The living body data measured by means of the living body measuring devices 10a to 10n are transmitted to the healthcare apparatus 100, while a response code that is indicative of the occurrence of communication failure, such as interruption of the data being received is transmitted from healthcare apparatus 100 to the living body measuring devices 10a to 10n. Further, the healthcare apparatus 100 and the external server 50 are connected by means of a telephone line or the like, and can transmit and receive data such as the living body data.

The following is a description of a method of using the data collection system shown in FIG. 1.

First, the user selects one of the living body measuring devices 10a to 10n and measures the living body data. For example, the user selects and switches on the weighing machine, and gets on the weighing machine to take a measurement. When the power is turned off after the measurement is finished, the measured living body data are transmitted to the healthcare apparatus 100 that is on standby for data reception. The healthcare apparatus 100 stores the received data. During the measurement, the healthcare apparatus 100 issues voices or animations for guidance as to the way of use of the weighing machine selected by the user. If a measurement is taken by means of another living body measuring device in like manner, the healthcare apparatus 100 gives guidance corresponding to the living body measuring device selected by the user during the measurement. When the individual living body measuring devices are switched off, the living body data are transmitted to the healthcare apparatus 100. The healthcare apparatus 100 stores the received living body data, and graphically displays the stored living body data on a display unit. The user can learn the tendency of variation of the living body data by watching the display unit. Thus, the healthcare apparatus 100 constitutes a data collection apparatus for collecting the living body data.

When the measurement by means of the living body measuring devices 10a to 10n is finished, the user transmits the living body data from the healthcare apparatus 100 to the external server 50. If a transmission switch of the healthcare apparatus 100 is operated, the living body data measured on that day are transmitted to the external server 50 of the hospital or caregiving center through the telephone line.

One of the living body measuring devices shown in FIG. 1 will now be described in detail with reference to FIG. 2.

The living body measuring device 10a comprises a control/operation unit 15, and power switch 11, living body sensing means 12, measurement switch 13, measurement failure determining means 14, storage means 16, transmission/reception means 17 and time measuring means 18, connected to the control/operation unit 15, respectively.

The control/operation unit 15 controls and operates the means 12, 13 and 16 to 18 in accordance with the operations of the power switch 11 and the measurement switch 13.

The power switch 11, which serves to turn on and off the living body measuring device 10a, is composed of a push-button switch, for example. The control/operation unit 15 controls the living body measuring device 10a so that the power is turned on if the power switch 11 is operated with the power off and that the power is turned off, on the other hand, if the power switch 11 is operated with the power on. Thus, the living body measuring device 10a is alternately switched on and off every time the power switch 11 is operated.

The living body sensing means 12 is means for detecting given living body data. It includes a cuff and a pressure sensor if the living body measuring device 10a is a sphygmomanometer, for example, and it is a thermister or the like if the device 10a is a clinical thermometer.

The measurement switch 13 is a switch for starting living body data measuring operation, and is composed of a push-button switch, for example. If the measurement switch 13 is operated with the living body measuring device 10a on, the control/operation unit 15 controls the respective operations of the living body sensing means 12, measurement failure determining means 14, storage means 16, transmission/reception means 17, and time measuring means 18. Thereupon, measuring operation is started.

The measurement failure determining means 14 determines whether or not the measurement is carried out correctly, taking into consideration the operation made during the time from the instant the living body measuring device 10a is switched on until the instant it is switched off or the measured living body data. For example, the measurement failure determining means 14 concludes the measurement to be a failure if the power switch 11 is depressed unexpectedly to turn off the power immediately before the start of the measurement or during the measurement or if a measured value much higher than a normal value Is detected.

The storage means 16 stores identification codes for identifying the living body measuring devices 10a to 10n and the living body data. The identification codes are stored in advance in the storage means 16. The living body data that are measured by means of the living body sensing means 12 are loaded into the storage means 16 through the control/operation unit 15.

The transmission/reception means 17 transmits the identification codes, living body data, and failure determination data (mentioned later) to the healthcare apparatus 100 by radio communication. The time measuring means 18 measures the time that elapses after the power is turned on by means of the power switch 11. The living body measuring device 10a has an automatic power-off function, and the control/operation unit 15 switches it from its power-on state over to its power-off state in accordance with the time measured by the time measuring means 18.

The following is a description of the power-on state and power-off state of the living body measuring device 10a.

In the power-on state, the control/operation unit 15 controls the living body sensing means 12, measurement failure determining means 14, transmission/reception means 17, and time measuring means 18 to render them nonoperating. In consequence, the measurement cannot be started even if the measurement switch 13 is depressed. If the living body measuring device 10a has display means, nothing is displayed on the display means.

If the power switch 11 is depressed to turn the power on, the control/operation unit 15 still continues to keep the living body sensing means 12, measurement failure determining means 14, transmission/reception means 17, and time measuring means 18 nonoperating (unless the measurement switch 13 is then depressed). If the measurement switch 13 is then depressed, the control/operation unit 15 can actuate the means 12, 14, 17 and 18, thereby starting the measurement.

The power switch 11 may also be used as the measurement switch 13. If the power switch 11 is depressed with the living body measuring device 10a off, in this case, the control/operation unit 15 actuates the living body sensing means 12, measurement failure determining means 14, transmission/reception means 17, and time measuring means 18, thereby allowing the measuring operation.

Figure 2:
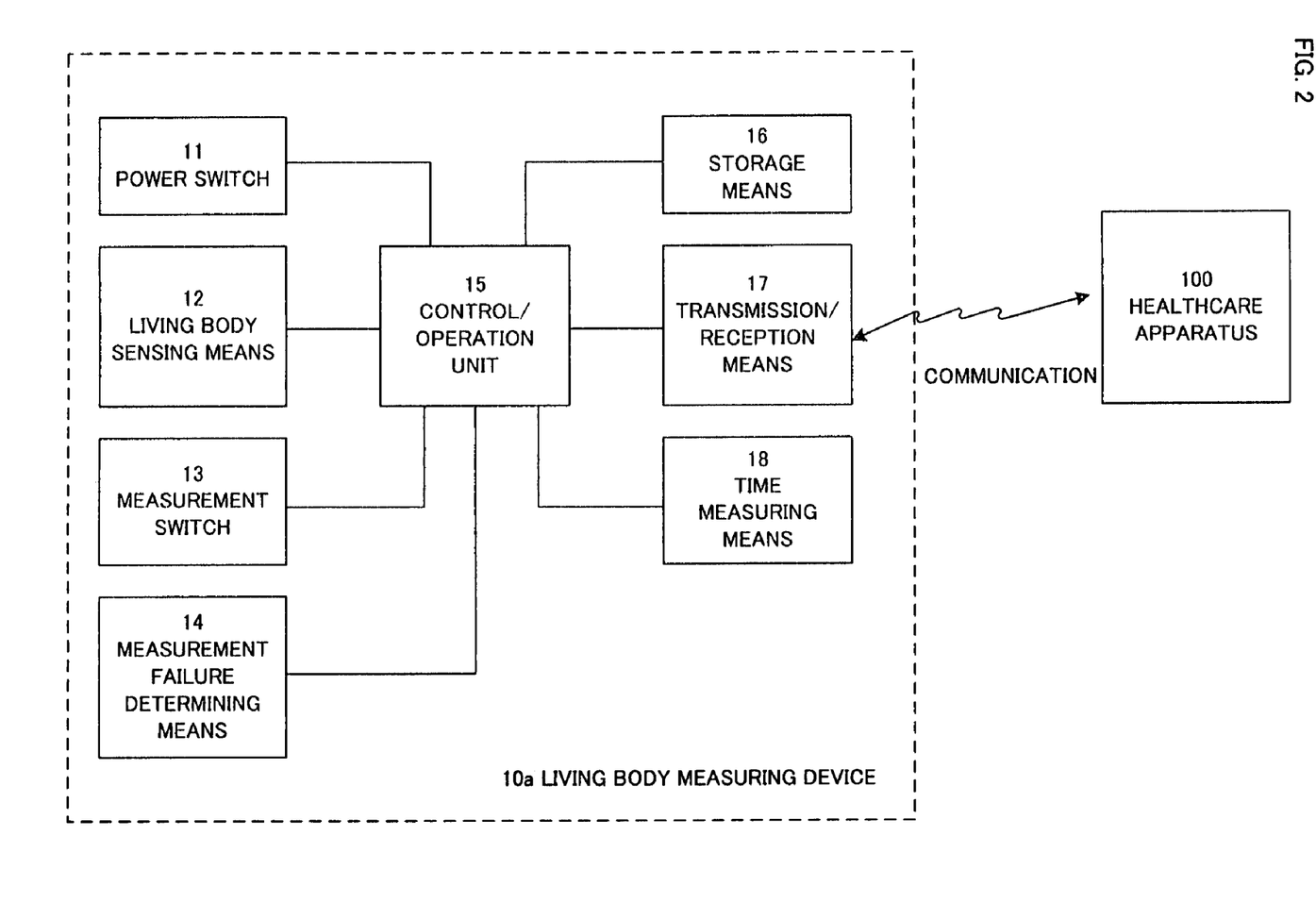
FIG. 2 is a block diagram showing components of a living body measuring device constituting the healthcare system of FIG. 1.

If the power switch 11 of the living body measuring device 10a shown in FIG. 2 is depressed to turn the power on, the control/operation unit 15 reads an identification code from the storage means 16, and controls the operation of the transmission means 17 to transmit the read identification code to the healthcare apparatus 100.

Alternatively, the control/operation unit 15 may be designed to read the identification code from the storage means 16 and control the operation of the transmission means 17 to transmit the read identification code to the healthcare apparatus 100 if the measurement switch 13 is further depressed after the power switch 11 is depressed to turn the power on.

If the power switch 11 is depressed to turn the power off, moreover, the control/operation unit 15 reads the identification code, living body data, and failure determination data from the storage means 16, and controls the operation of the transmission means 17 to transmit the read information to the healthcare apparatus 100.

While the above description is a description of one (living body measuring device 10a) of the living body measuring devices shown in FIG. 1, the remaining living body measuring devices 10b, . . . 10n are constructed in the same manner as the living body measuring device 10a.

Figure 3:
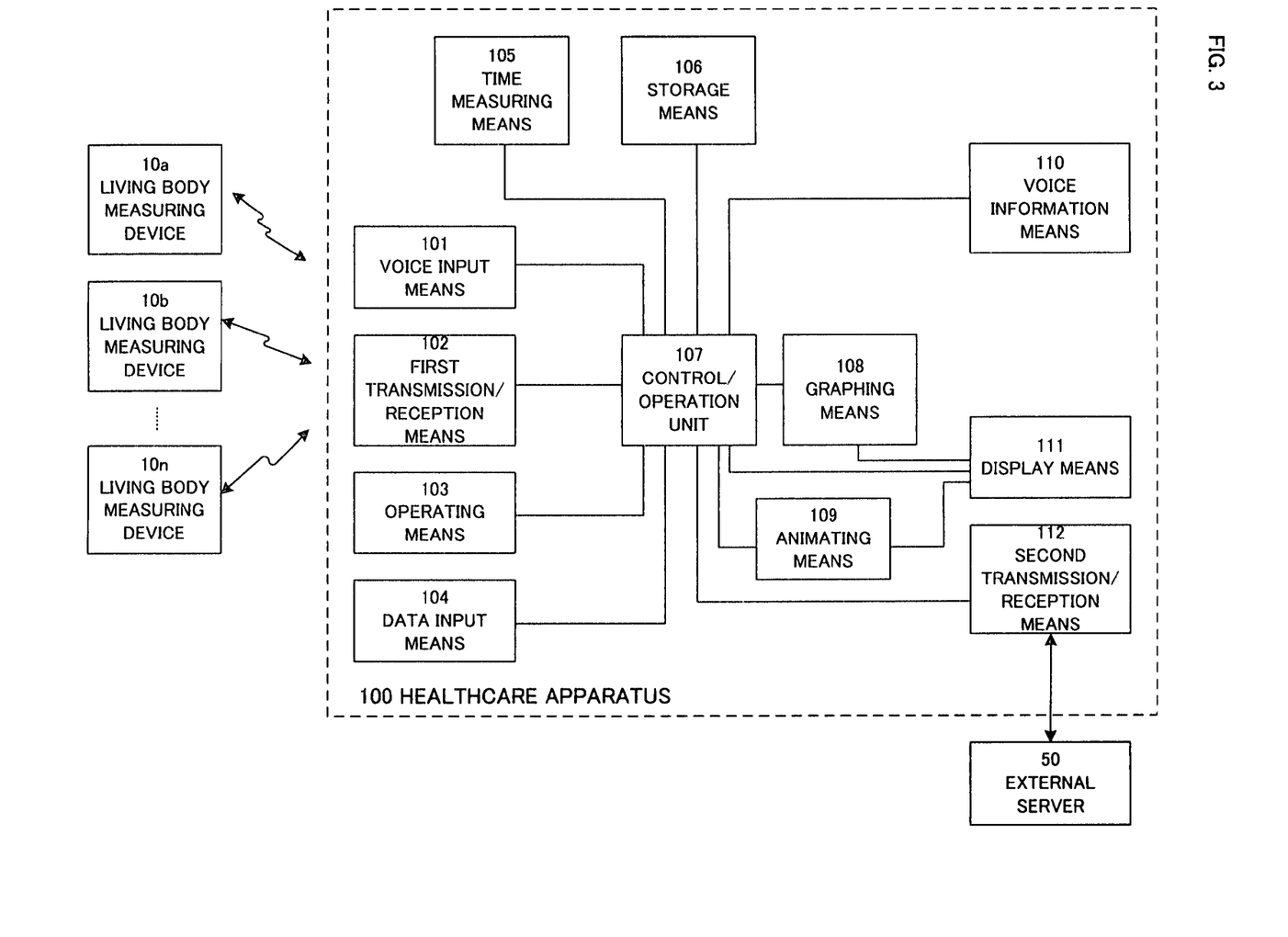
FIG. 3 is a block diagram showing components of a healthcare apparatus constituting the healthcare system of FIG. 1.

The healthcare apparatus 100 of FIG. 1 will now be described further in detail with reference to FIG. 3.

The healthcare apparatus 100 has a control/operation unit 107 and voice input means 101, first transmission/reception means 102, operating means 103, data input means 104, time measuring means 105, storage means 106, graphing means 108, animating means 109, voice information means 110, display means 111, and second transmission reception means 112 that are individually connected to the control/operation unit 107.

The control/operation unit 107 controls the individual mans that are connected to the control/operation unit 107 in accordance with the respective operations of the voice input means 101, operating means 103, and data input means 104, data received by the first transmission/reception means 102, etc. The voice input means 101 is means for receiving a voice uttered by the user. The control/operation unit 107 recognizes the voice inputted through the control/operation unit 107. If the voice can be recognized, the control/operation unit 107 carries out a process according to the voice.

The first transmission/reception means 102 receives the identification code, living body data, and failure determination data transmitted from the living body measuring devices 10a to 10n and transmits the response code to the living body measuring devices 10a to 10n. The response code indicates the occurrence of communication failure, such as interruption of the data being received. The operating means 103 is composed of a mouse or operating switch, for example, and serves to turn on and off the healthcare apparatus 100, executes mode switching operation of a living body data reception mode, detail setting mode, center transmission mode, user selection mode, etc., and carries out operations in the individual modes.

The data input means 104 is composed of a character key or numeric key, and is used to input a user number for the use of the healthcare apparatus 100. The storage means 106 stores the living body data received by the first transmission/reception means 102. The living body data for several months are stored day by day in the storage means 106. The graphing means 108 graphs the living body data that are stored in the storage means and are displayed on the display means 111. The display means 111 graphically displays the living body data and further displays animations for guidance (mentioned later), an input setting picture for the user number, etc.

The animating means 109 and the voice information means 110 give guidance to the user as to an operating method, a measuring method for the living body measuring devices 10a to 10n, etc. The animating means 109 displays animations and the like on the display means 111. The voice information means 110 is composed of a speaker, and gives voice information.

The second transmission/reception means 112 is mans for transmitting to and receiving data from the external server 50. It transmits the living body data or the like to the external server 50 and receives message data or the like from the external server 50.

If the control/operation unit 107 switches the first transmission/reception means 102 to a reception state, the healthcare apparatus 100 is brought to the living body data reception mode. As this is done, the first transmission means 102 receives the living body data, identification code, and failure determination data from the living body measuring devices 10a to 10n, stores the received data in the storage means 106, and carries out a process corresponding to the received contents. If operation by means of the voice input means 101 or the operating means 103 is performed in the living body data reception mode, moreover, a process corresponding to the operation is carried out.

The following is a specific description of the data (identification code, living body data, and failure determination data) which the living body measuring devices 10a to 10n transmits to the healthcare apparatus 100.

The identification code for identifying each of the living body measuring devices 10a to 10n is composed of three English characters, e.g., "BUY" for the weighing machine, "WAM" for the body-fat meter, etc., which never overlap one another. If the healthcare apparatus 100 receives the identification code "BUY", for example, it concludes that the living body measuring device by which the identification device is transmitted is the weighing machine.

Each living body data is composed of a number of a given number of figures for each of the living body measuring devices 10a to 10n. If a measured value obtained by means of each of the living body measuring devices 10a to 10n contains no decimal-place figures, the measured value is regarded directly as the living body data. If the measured value contains any decimal-place figure or figures, on the other hand, it is multiplied by ten or one hundred to be changed into a number that contains no decimal point, and the resulting number is regarded as the living body data. If the pulse rate value measured by means of the sphygmomanometer is 73 pulses/minute, for example, "073" is regarded as the living body data of the sphygmomanometer. If the weight measured by means of the weighing machine is "65.5 kg", moreover, "0655", a number of four figures obtained by multiplying the value by ten, is regarded as the living body data of the weighing machine.

The failure determination data is composed of one alphabetical character. If the measuring operation is carried out normally and the measured value is within an ordinary range, failure determination data "A" is outputted. If the power of the measuring device is turned off before the measurement is started after the power is turned on, on the other hand, failure determination data "B" is outputted. If the measured value is not lower than a preset upper limit or not higher than a preset lower limit (i.e., if the measured value is not within the ordinary range) when the measurement is started, failure determination data "E" is outputted. For other cases, failure determination data "C", "D", "F", . . . are suitably outputted depending on the type of the measurement failure.

When the healthcare apparatus 100 receives the living body data to which the failure determination data "A" is applied from the living body measuring devices 10a to 10n, therefore, the living body data is restored to the measured value (e.g., reduced to ⅒ to have a decimal point) and loaded into the storage means 106. When the living body data to which any other failure determination data than "A" are received from the living body measuring devices 10a to 10n, measured values corresponding to the living body data are not loaded into the storage means 106.

Figure 4:
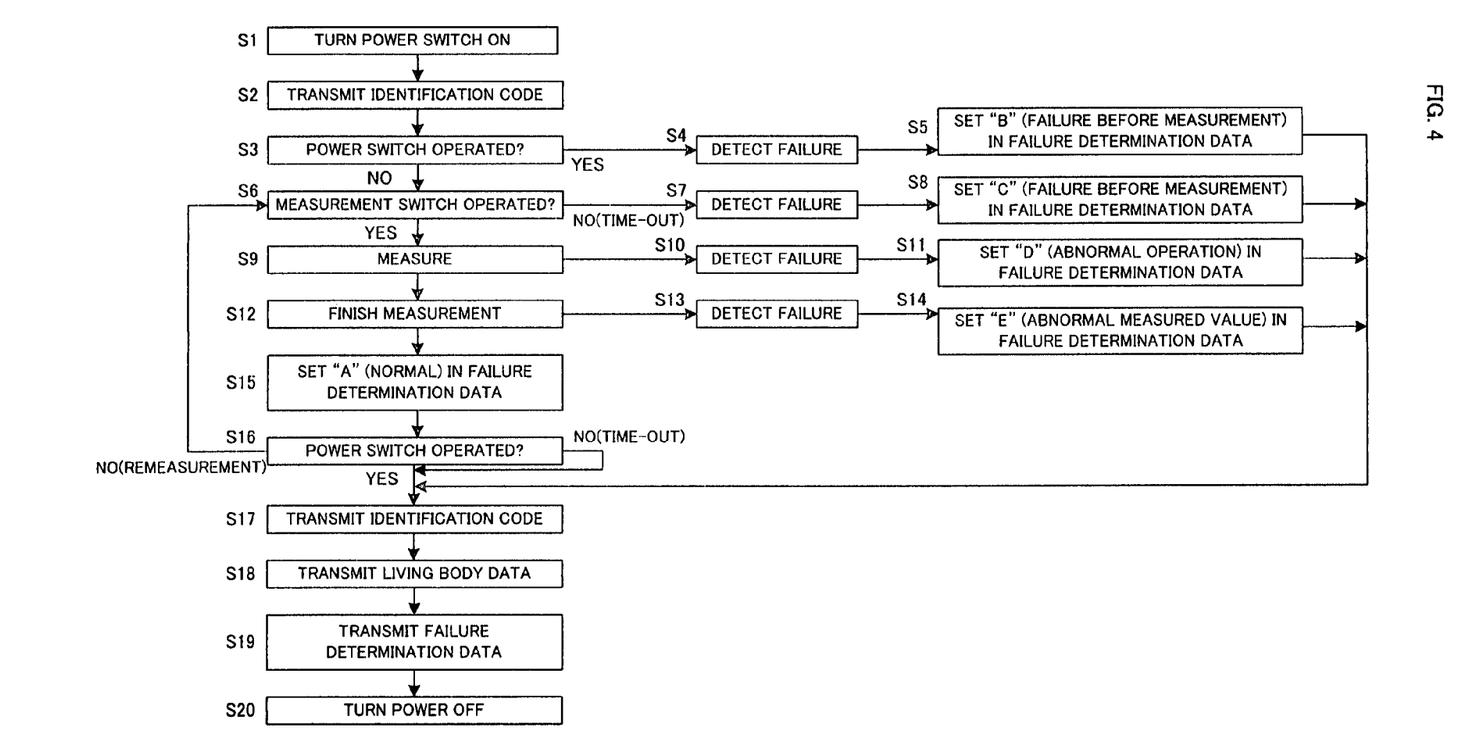
FIG. 4 Is a flowchart for explaining the measuring operation of the living body measuring device shown in FIG. 2.

The measuring operation of the living body measuring device will now be described with reference to FIGS. 2 and 4. In the description to follow, the user is supposed to select the sphygmomanometer 10a from the living body measuring devices 10a to 10n, by way of example, and carry out the measuring operation. In the flowchart of FIG. 4, symbols S1 to S20 designate various processes (steps) of the living body measuring device 10a.

First, the power switch 11 of the living body measuring device 10a, a sphygmomanometer, is operated (S1). Thereupon, the living body measuring device 10a is switched on to become ready for the measurement. When the power is turned on, the transmission/reception means 17 of the selected living body measuring device 10a transmits an identification code that indicates that its own living body measuring device is a sphygmomanometer (S2).

When the healthcare apparatus 100 receives this identification code, the healthcare apparatus 100 uses a voice and/or animation to carry out operation for guidance related to the way of using the living body measuring device that is specified by the identification code, as mentioned later. If the healthcare apparatus 100 receives the identification code for the sphygmomanometer, for example, it voices "PUT ON CUFF" and displays an animation of a figure on a display screen. Thereupon, a measurer can wind the cuff around an arm to be ready for the measurement in accordance with the guidance.

If the identification information is transmitted by turning on the power switch 11 in this manner, the identification code can be automatically transmitted to the healthcare apparatus 100 to serve for the guidance as the user only carries out necessary operation for the execution of the measuring operation without operating a dedicated switch for the transmission of the identification code. Thus, troublesome operation for transmission become unnecessary.

Further, the same effect can be obtained if the identification code is transmitted when the operation for starting the measuring operation is carried out by means of the measurement switch 13 in the aforesaid manner.

Then, the control/operation unit 15 determines whether or not the power switch 11 is operated (S3) (after the identification information is transmitted in the preceding step S2). If it is concluded that the power switch 11 is not operated, the control/operation unit 15 then determines whether or not the measurement switch 13 is operated (S6). If it is concluded in this step that the measurement switch 13 is operated, then the measuring operation is started (S9). Thereupon, compressed air is fed into the cuff, and the pressure inside the cuff is detected by means of the pressure sensor. When the measurement is finished (S12) after the measuring operation is carried out normally, the measurement failure determining means 14 concludes that the measurement is carried out normally, and sets "A", which is indicative of normal execution of the measurement, in the failure determination data to be transmitted together with the living body data to the healthcare apparatus 100 (S15).

After "A" is set in the failure determination data (S15) after the measurement is thus finished (S12), the control/operation unit 15 determines whether or not the power switch 11 is operated (S16).

If it is concluded in this step that the power switch 11 is operated (i.e., that the power is turned off because the measurement is finished), the transmission/reception means 17 transmits the identification code that identifies the sphygmomanometer (S17), then transmits the living body data corresponding to the measured value obtained in S9 (S18), and Further transmits the failure determination data ("A" in this case) (S19). When these pieces of information are transmitted, the control/operation unit 15 controls the respective operations of the individual means and switches off the living body measuring device 10a.

The time measuring means 18 measures the time that elapses after the measurement is finished in S12. If it is concluded in S16 that the power switch 11 is not operated within a predetermined time, the program automatically advances to S17, whereupon the processes of S17 to S20 are carried out. Thus, although the measurement is normally carried out and finished (S9–S12–S15), the identification code, living body data, and failure determination data are automatically transmitted from the transmission/reception means 17 by the automatic power-off function unless the power switch 11 is depressed within a given time (e.g., 5 minutes) subsequent to the termination of measurement ("No" in S16). If the living body data are transmitted as the living body measuring device is switched from the power-on state over to the power-off state (or by the automatic power-off function) in this manner, the user can transmit the data without performing any special operation for transmitting the living body data.

The following is a description of the case where any other data than "A" which is indicative of normality is set in the failure determination data. The other failure determination data than "A" can be set only during the time from the instant the power switch 11 is turned on in S1 until the instant the power switch 11 is turned off in S16.

If the control/operation unit 15 concludes that the power switch 11 is depressed to turn off the power before the measurement switch is operated (S6) after the power is turned on by means of the power switch 11 in S1 ("Yes" in S3), the measurement failure determining means 14 concludes that the operation is abnormal (S4), and sets "B", which indicates that the power is turned off before the measurement is started, in the failure determination data (S5).

If the control/operation unit 15 detects that the measurement switch has not been operated within a predetermined time (e.g., 5 minutes) after the power switch 11 is turned on in S1 ("No" in S6), it is concluded that the operation is abnormal (S7). The measurement failure determining means 14 sets "C", which indicates that the measurement switch 13 has not been depressed within the given time (or the power is automatically turned off before the measurement is carried out), in the failure determination data (S8). The time measuring means 18 measures the time that elapses after the power switch 11 is turned on in S1.

If the control/operation unit 15 concludes that the operation during the measurement in S9 (S10) is abnormal or if the cuff is pressurized for too long a time, for example, the measurement failure determining means 14 sets "D", which indicates that the measuring operation is abnormal, in the failure determination data (S11).

If the obtained measured value exceeds a preset range (i.e., if the measured value is not lower than a preset upper limit or not higher than a preset lower limit) although the measurement is finished in S12, moreover, the control/operation-unit 15 concludes that the measured value is not a reliable value (S13). In consequence, the measurement failure determining means 14 sets "E", which indicates that the measured value is an abnormal value, in the failure determination data (S14).

After the failure determination data "B", "C", "D" or "E" is set in S5, S8, S11 or S14, the aforesaid processes S17 to S20 are carried out. More specifically, if the measurement failure determining means 14 concludes that the measurement is not normal, the identification code, living body data, and failure determination data can be automatically transmitted to turn off the living body measuring device without the measurer's power-off operation.

In another case, the control/operation unit 15 concludes in S10 that the operation is abnormal if the voltage of a battery is reduced below a given level during the measurement in the living body measuring devices 10a to 10n. In still another case, the control/operation unit 15 concludes in S14 that the operation is abnormal if the measured value of the clinical thermometer is deviated from the range from 32 to 42 degrees centigrade or if the measured value of the body-fat meter is deviated from the range from 5% to 50%.

In the measuring operation of the living body measuring device shown in the flowchart of FIG. 4, the failure determination data is always transmitted in S19. Alternatively, the failure determination data may be transmitted in S19 only if it is concluded in S4, S7, S10 or S13 that the operation is abnormal, while the failure determination data is not transmitted if "A" is set in the failure determination data in S15.

In the measuring operation of the living body measuring device shown in the flowchart of FIG. 4, moreover, the living body data obtained by the measurement is always transmitted in S18. Alternatively, the living body data may be allowed to be transmitted only when "A" is set in the failure determination data in S15. In this case, the living body data are not transmitted (or the process of S18 is skipped) if any other data than "A" is set in the failure determination data.

Figure 5:
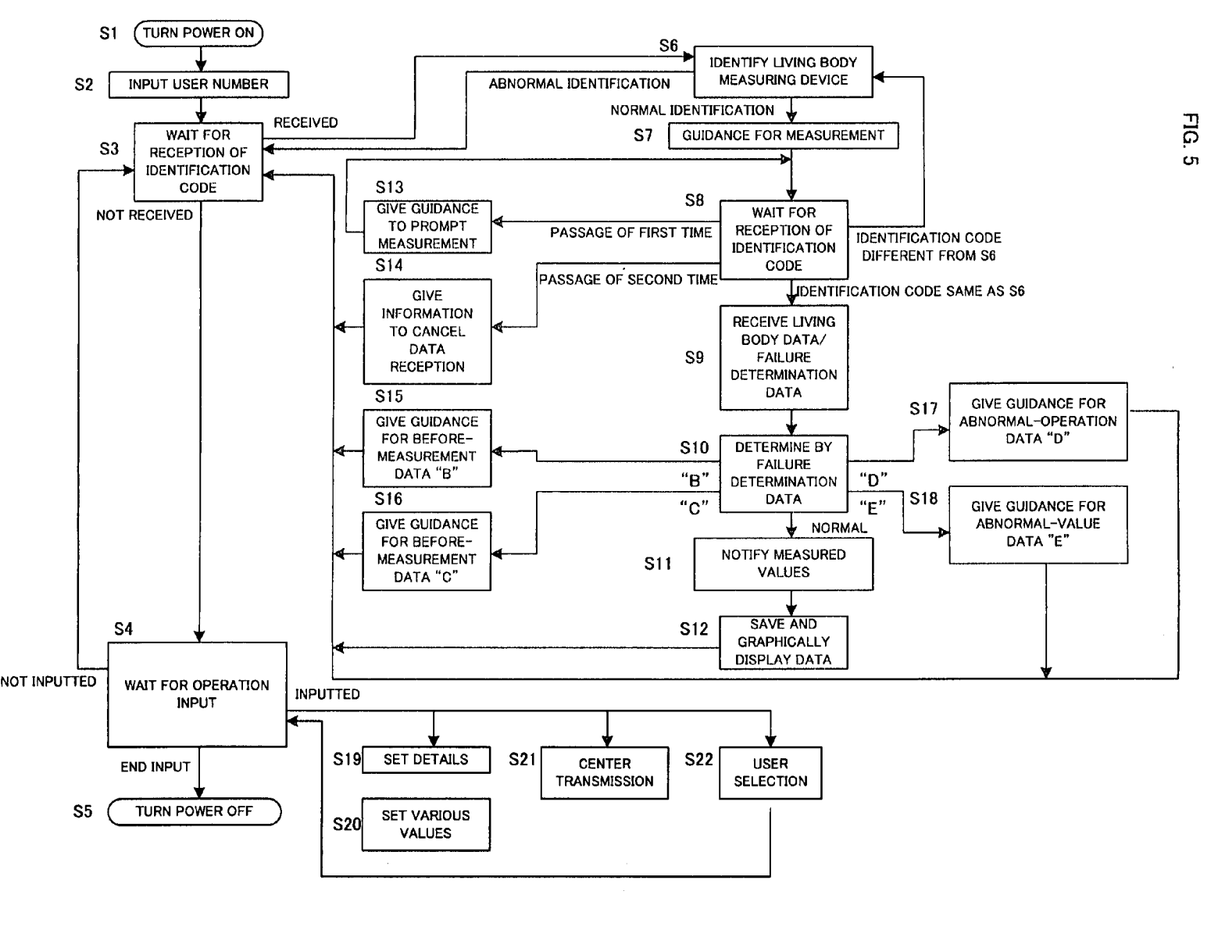
FIG. 5 is a flowchart for explaining the operation of the healthcare apparatus shown in FIG. 3.

The operation of the healthcare apparatus will now be described with reference to FIGS. 3 and 5. In the flowchart of FIG. 5, symbols S1 to S22 designate various processes (steps) of the healthcare apparatus 100.

First, the operating means 103 is operated to switch on the healthcare apparatus 100 (S1). Then, the operating means 103 is operated to input the user number (S2). A plurality of users can use the healthcare apparatus 100, and a user number is assigned to each user. When the user number is inputted in S2, the first transmission/reception means 102 stands ready to receive the identification code from the living body measuring devices 10a to 10n (S3). If no identification code is then received, operation input through the voice input means 101 or the operating means 103 is awaited (S4). If there is no operation input, the program returns to S3. The process of S3 and the process of S4 are repeated (identification code reception wait mode). If the power is turned off by means of the operating means 103 in S4, the healthcare apparatus 100 is switched off, whereupon the operation is finished.

If the power switch 11 in any of the living body measuring devices 10a to 10n is depressed (or if the process of S1 in the flowchart of FIG. 4 is carried out), an identification code that specifies the living body measuring device is transmitted from it to the healthcare apparatus 100 (S2 in the flowchart of FIG. 4).

When the healthcare apparatus 100 receives this identification code (S3), the control/operation unit 107 identifies the type of the living body measuring devices 10a to 10n in accordance with the identification code (S6). More specifically, the unit 107 identifies the sphygmomanometer, weighing machine, body-fat meter, or clinical thermometer from which the identification code is transmitted. If the type of the living body measuring devices 10a to 10n is identified normally, operation for guidance as to the way of using the identified living body measuring device is carried out (S7). For example, the voice information means 110 gives a guidance "PUT ON CUFF" (sphygmomanometer) or "GET ON WEIGHING MACHINE" (weighing machine), and the animating means 109 also gives a guidance on the display means 111. Thus, as the user turns on the power switch 11 of any of the living body measuring devices 10a to 10n, the healthcare apparatus 100 gives a guidance corresponding to the measuring device that is used by the user. If the identification code cannot be normally identified in S6, the program returns to S3 for the reception wait mode.

After the measurement guidance is given in S7, reception of the identification code from the living body measuring devices 10a to 10n is awaited in S8. If the user operates the same living body measuring device identified in S6 (i.e., if the processes of S3 to S20 in the flowchart of FIG. 4 are carried out for that living body measuring device), the identification code is transmitted from that living body measuring device to the healthcare apparatus 100 in S17 in the flowchart of FIG. 4.

When this is done, the healthcare apparatus 100 is in the identification code reception wait mode (S8). It receives the transmitted identification code and determines whether or not the received identification code is identical with the identification code that is previously received in S6. If it is concluded that the identification code is identical, the living body data and the failure determination data from the living body measuring device transmitted in the processes of S18 and S19 in the flowchart of FIG. 4 are received (S9).

If the user operates the power switch 11 of the measuring device different from the living body measuring device that is previously identified in S6, thereby switching on the device, with the healthcare apparatus 100 kept in the identification code reception wait mode, on the other hand, an identification code different from the identification code that is previously identified in S6 is transmitted from the living body measuring device concerned to the healthcare apparatus 100 in S8 (S2 in the flowchart of FIG. 4). Thereupon, the healthcare apparatus 100 receives this identification code (S8), concludes that the identification code just received is different from the Identification code previously received in S3, and returns to S6 without carrying out the aforesaid process in S9. Then, the type of the living body measuring device is identified in accordance with the secondly received identification code. If it is identified normally, the aforesaid guidance is given (S7). If it is not identified normally, the program goes to S3, whereupon the identification code is awaited.

Thus, the healthcare apparatus 100 receives the identification code after confirming that the living body data fed from the living body measuring device in the process of S18 in the flowchart of FIG. 4 are the living body data of the living body measuring device that is identified by the identification information transmitted in S17 in the same flowchart of FIG. 4, in the processes of S8 and S6. If the power switch 11 of another living body measuring device is turned on before measurement on one living body measuring device is finished after the power switch 11 of the one living body measuring device is turned on, moreover, the living body data measured by means of that living body measuring device which is switched on later are expected to be acquired.

Thus, the healthcare apparatus 100 receives the identification code when receiving the living body data and also receiving the identification code when selecting the living body measuring device. It is ensured, therefore, that the received living body data are delivered from the selected living body measuring device, so that the reliability of the living body data reception increases.

Further, the time measuring means 105 measures the time having elapsed after the reception of the identification code in S6. If the healthcare apparatus 100 receives no identification code within a first time (e.g., 3 minutes) in S8, Information is given to prompt measurement (S13). The voice information means 110 gives information "NOT MEASURED YET, START MEASUREMENT", for example. This is a guidance to inform the measurer of the fact that the measurement switch 13 is not depressed yet with the power switch 11 of the living body measuring device turned on by the measurer and to prompt the measurement. For this guidance to prompt the measurement, a message to the same effect may be displayed on the display means 111 in place of the voice, or "REMEASURE" may be displayed on the display means 111.

If no identification code is received within a second time (e.g., 7 minutes) after the passage of the first time in S8, information is given to cancel the reception of the living body data from the living body measuring device of which the power switch 11 is turned on (S14), and the program returns to the process of S3. The voice information means 110 gives information "NO MEASURED VALUE RECEIVED, START MEASUREMENT AGAIN FROM BEGINNING", for example. This second time is longer than a given time (5 minutes in the aforesaid example) of which the passage is determined after the power switch 11 of the living body measuring device is depressed in S16 in the flowchart of FIG. 4. Thus, after the power is automatically turned off with the measurement switch 13 not depressed despite the passage of the given time (5 minutes) after the power switch 11 of the specific living body measuring device is turned on, the voice information means 110 of the healthcare apparatus 100 gives information to that effect.

Then, the failure determination data, transmitted from the living body measuring device in S19 in the flowchart of FIG. 4, is received (S10), and its content is checked. The following is a description of the results.

(1) If "B" is found to be set in the failure determination data, it is concluded that the power switch 11 of the specific living body measuring device is turned off before the measurement is started (or while the measurement switch 13 is not depressed) with the power switch on, and a guidance to that effect is given (S15). The voice information means 110 gives information "SPHYGMOMANOMETER IS SWITCHED OFF BEFORE MEASUREMENT, MEASURE AGAIN", for example.

(2) "C" is found to be set in the failure determination data, it is concluded that the power switch 11 of the specific living body measuring device is automatically turned off, since the measurement switch 13 is not depressed (or the measurement is not started) despite the passage of a given time after the power switch is turned on, and a guidance to that effect is given (S16). The voice information means 110 gives information "SPHYGMOMANOMETER IS AUTOMATICALLY SWITCHED OFF BEFORE MEASUREMENT, MEASURE AGAIN", for example.

(3) If "D" is found to be set in the failure determination data, it is concluded that the measuring operation is abnormal although the measurement is started by means of the specific living body measuring device, and a guidance to that effect is given (S17). The voice information means 110 gives information "NOT MEASURED CORRECTLY, MEASURE AGAIN", for example.

(4) If "E" is found to be set in the failure determination data, it is concluded that the measuring method is wrong, since the measured value is a value that could not be obtained by normal measurement although the measured value is stored after the measurement is carried out by means of the specific living body measuring device, and a guidance to that effect is given (S18). For example, Information "ABNORMAL MEASURED VALUE, MEASURE AGAIN BY CORRECT MEASURING METHOD" is given.

(5) If "A" is found to be set in the failure determination data, it is concluded that the measurement is carried out normally by means of the specific living body measuring device, and a guidance to that effect is given (S18). The voice information means 110 gives information "MEASUREMENT IS FINISHED, MEASURED VALUES: MAXIMUM BLOOD PRESSURE OF 125 mmHg AND MINIMUM BLOOD PRESSURE OF 76 mmHg", for example, and the values of the living body data that are transmitted from the living body measuring device in S18 in the flowchart of FIG. 4 are notified (S11). This measured value is stored in the storage means 106 and graphically displayed on the display means 111 by means of the graphing means 108 (S12). When the processes of S12, S15, S16, S17 and S18 are finished, the program returns to S3 for the reception wait mode, whereupon the reception wait mode of the living body measuring device identified in S6 is canceled.

If user selecting operation, center transmitting operation, and detail setting operation are carried out in the operation input wait process of S4 by means of the voice input means 101 or the operating means 103, moreover, the program advances to the user selection mode (S22), center transmission mode (S21), and detail setting mode (S19), whereupon the user selecting operation, center transmitting operation, and various setting operations (S20) are carried out. When these operations are finished, the program returns to S4 for the operation input wait mode. If power-off operation is carried out by means of the voice input means 101 or the operating means 103 in S4, the healthcare apparatus 100 is switched off, whereupon the operation terminates (S5).

In the healthcare system to which the data collection system according to the present invention is applied, as shown in FIG. 1, the communication between the living body measuring devices 10a to 10n and the healthcare apparatus 100 is radio communication. Alternatively, however, the living body measuring devices 10a to 10n and the healthcare apparatus 100 may be connected in a wired manner by means of connecting wires. Thus, the present invention is applicable without regard to the form of transmission only if data can be transmitted from the living body measuring devices 10a to 10n to the healthcare apparatus 100.

According to the present embodiment, moreover, the guidance of the living body measuring device corresponding to the identification code is carried out in a manner such that the healthcare apparatus 100 receives the identification code from the living body measuring devices 10a to 10n. Alternatively, however, the healthcare apparatus 100 may be designed to control the environment of measurement depending on the type of the living body measuring devices 10a to 10n instead of carrying out the guidance, for example. The healthcare apparatus 100 may, for example, be designed automatically to switch off peripheral apparatuses such as a TV set that easily produces noises if the identification code of a living body measuring device such as an electrocardiograph that is susceptible to surrounding electromagnetic and electrostatic noises is received. Further, the healthcare apparatus 100 may be designed to measure the room temperature to see if it is suited for the measurement or control an air conditioner in accordance with the measured temperature if the identification code of a living body measuring device such as a clinical thermometer that is influenced by the room temperature.

The operation for guidance as to the way of using the living body measuring devices 10a to 10n is intended for users who are not familiar with the method of use. If the user is bound, for example, to start guidance operation by manipulation on the side of the healthcare apparatus 100, which is not the case with the embodiment described with reference to FIGS. 1 to 5, operation for starting the guide in the healthcare apparatus 100 must be performed with every measurement in each of the living body measuring devices 10a to 10n.

According to the embodiment described with reference to FIGS. 1 to 5, on the other hand, the operation for guidance as to the way of using the living body measuring devices 10a to 10n is carried out by means of the healthcare apparatus 100, whereas the operation for starting the guidance operation is carried out on the side of the living body measuring devices 10a to 10n, so that the user can enjoy simple manipulation and high user-friendliness.

The invention claimed is:

1. A data collection system comprising a plurality of measuring devices that transmit identification information for discriminating a measuring device and measured values and a data collection apparatus for receiving and storing the identification information and measured values transmitted from the measuring devices, wherein each measuring device automatically transmits the identification information when said measuring device is manipulated to start a measuring operation, and the data collection apparatus receives the identification information transmitted by any one of the measuring devices, discriminates the measuring device corresponding to the received identification information from among the plurality of measuring devices, and gives guidance as to the way of using the discriminated measuring device corresponding to the received identification information.

2. The data collection system according to claim 1, wherein the data collection apparatus selects one measuring device from among said plurality of measuring devices in accordance with the received identification information and is brought to a reception state in which the apparatus receives only the measured value transmitted from the selected measuring device.

3. The data collection system according to claim 2, wherein the measuring device transmits a combination of identification information and the measured value.

4. The data collection system according to claim 3, wherein the data collection apparatus receives the measured value only when the identification information combined with the measured value is identical with the identification information representative of the selected measuring device.

5. The data collection system according to claim 2, wherein the data collection apparatus cancels the selection on receiving the measured value.

6. The data collection system according to claim 1, wherein said manipulation to start a measuring operation is a manipulation for switching on the measuring device.

7. A data collection system comprising a plurality of measuring devices that transmit identification information and measured values anti a data collection apparatus for receiving and storing the identification information and measured values transmitted from the measuring devices, wherein the data collection apparatus receives the identification information transmitted by any one of the measuring devices, selects one measuring device from among said plurality of measuring devices in accordance with the received identification information, brings itself to a reception state in which the apparatus receives only the measured value transmitted from the selected measuring device, gives guidance as to the way of using the selected measuring device corresponding to the received identification information, and cancels the selection on receiving the measured value.

8. The data collection system according to claim 2 or 7, wherein the data collection apparatus is brought to a reception state in which the apparatus receives only the measured value transmitted from a measuring device corresponding to identification information different from the identification information representative of the selected measuring device if the identification information different from the identification information representative of the selected measuring device is received in said reception state.

9. The data collection system according to claim 2 or 7, wherein the data collection apparatus gives information to prompt measurement for the selected measuring device if no identification information is received from the selected measuring device within a first time subsequent to the selection of the measuring device.

10. The data collection system according to claim 2 or 7, wherein the data collection apparatus cancels the selection of the measuring device if no identification information is received from the selected measuring device within a second time after the passage of the first time subsequent to the selection of the measuring device.

11. The data collection system according to claim 2 or 7, wherein the measuring device has an automatic power-off function to turn off the power automatically when given conditions are met with the power on, and the data collection apparatus gives information to prompt the measurement before the selected measuring device is switched off by the automatic power-off function.

12. The data collection system according to claim 1 or 7, wherein said guidance is given in the form of voice message and/or animation display.

* * * * *

UNITED STATES PATENT AND TRADEMARK OFFICE
CERTIFICATE OF CORRECTION

PATENT NO. : 7,191,075 B2  
APPLICATION NO. : 10/492126  
DATED : March 13, 2007  
INVENTOR(S) : Hideki Shimizu Page 1 of 1

It is certified that error appears in the above-identified patent and that said Letters Patent is hereby corrected as shown below:

In column 14, line 38, please change "anti" to --and--.

Signed and Sealed this

Fifth Day of June, 2007

JON W. DUDAS  
*Director of the United States Patent and Trademark Office*